(12) United States Patent
Kochelek et al.

(10) Patent No.: US 8,893,813 B2
(45) Date of Patent: Nov. 25, 2014

(54) FIRE PROTECTION SPRINKLER SYSTEM WITH OXYGEN CORROSION SENSITIVE COUPON ASSEMBLY AND METHOD OF MONITORING CORROSION IN A FIRE PROTECTION SPRINKLER SYSTEM

(75) Inventors: Jeffrey T. Kochelek, Creve Coeur, MO (US); David J. Burkhart, Wentzville, MO (US)

(73) Assignee: Engineered Corrosion Solutions, LLC, St. Louis, MO (US)

( * ) Notice: Subject to any disclaimer, the term of this patent is extended or adjusted under 35 U.S.C. 154(b) by 248 days.

(21) Appl. No.: 13/197,925

(22) Filed: Aug. 4, 2011

(65) Prior Publication Data

US 2012/0031629 A1    Feb. 9, 2012

Related U.S. Application Data

(60) Provisional application No. 61/371,328, filed on Aug. 6, 2010.

(51) Int. Cl.
*A62C 35/00*      (2006.01)
*A62C 35/68*      (2006.01)
*G01N 17/04*     (2006.01)

(52) U.S. Cl.
CPC ............... *A62C 35/68* (2013.01); *G01N 17/043* (2013.01)
USPC .................................................. 169/16; 169/5

(58) Field of Classification Search
CPC ........ A62C 35/00; A62C 35/58; A62C 35/60; A62C 35/68
USPC ................ 169/5, 17, 18, 23; 239/71, 77, 450; 73/779

See application file for complete search history.

(56) References Cited

U.S. PATENT DOCUMENTS

| | | | |
|---|---|---|---|
| 3,490,271 A | 1/1970 | Hays | |
| 3,942,546 A * | 3/1976 | Radd et al. | 137/93 |
| 4,575,678 A * | 3/1986 | Hladky | 205/776 |
| 4,683,035 A * | 7/1987 | Hunt et al. | 205/777 |
| 4,945,758 A | 8/1990 | Carpenter | |
| 5,171,524 A * | 12/1992 | Niolon | 422/53 |
| 6,277,329 B1 * | 8/2001 | Evans | 422/80 |
| 8,470,423 B2 * | 6/2013 | Jarvenkyla | 428/36.91 |
| 2004/0231862 A1 | 11/2004 | Kirn et al. | |
| 2009/0068060 A1 | 3/2009 | Alfermann et al. | |

* cited by examiner

*Primary Examiner* — Davis Hwu
(74) *Attorney, Agent, or Firm* — Harness, Dickey & Pierce, P.L.C.

(57) ABSTRACT

A fire protection sprinkler system and method of monitoring corrosion in a fire protection sprinkler system that includes a pipe network and at least one sprinkler connected with said pipe network. A corrosion monitor assembly is provided in the pipe network that includes at least one metal coupon and an oxygen depletion area defined on a surface portion of the coupon. A mounting member positions the corrosion monitor assembly to be at least partially covered with water when the sprinkler system is in an operative state.

26 Claims, 3 Drawing Sheets

FIRE PROTECTION SPRINKLER SYSTEM WITH OXYGEN CORROSION SENSITIVE COUPON ASSEMBLY AND METHOD OF MONITORING CORROSION IN A FIRE PROTECTION SPRINKLER SYSTEM

CROSS REFERENCE TO RELATED APPLICATION

This application claims priority from U.S. provisional patent application Ser. No. 61/371,328, filed on Aug. 6, 2010, the disclosure of which is hereby incorporated herein by reference in its entirety.

BACKGROUND OF THE INVENTION

The present invention is directed to a technique for monitoring corrosion in a fire protection sprinkler system and, in particular, to such a technique utilizing coupons positioned in the system during use and subsequently removed for inspection. The invention finds application in both a wet pipe fire protection sprinkler system and in a dry fire protection sprinkler system.

The presence of standing water in fire protection sprinkler systems typically leads to corrosion in the piping network, valves, and the like. If left undetected, such corrosion may eventually lead to pitting and pinholes in the piping network and even system failure.

There are two general types of fire protection sprinkler systems. In a wet pipe fire protection sprinkler system, water is present under pressure at all times throughout the system. Therefore, when the fuse of a sprinkler head is actuated by heat, or the like, water is immediately discharged from the sprinkler head to extinguish the fire. Wet pipe sprinkler systems are typically used in areas that are heated so that the temperature does not drop below freezing, which could damage the system. In a dry fire protection sprinkler system, an electrically actuated valve or a pressurized gas holds water back from the pipe network, which is maintained generally free of all but a residual amount of water.

Dry fire protection sprinkler systems come in two varieties—dry pre-action fire protection sprinkler systems and dry pipe fire protection sprinkler systems. In a dry pre-action fire protection sprinkler system, an electrically or pneumatically operated valve holds water back from the piping network. A smoke or heat detector operates the valve when a fire condition exists in order to flood the piping network with water. The water is discharged when a sprinkler head is actuated by heat. Maintenance air may optionally be supplied under pressure to the piping network in the dry pre-action fire protection sprinkler system to allow monitoring of air pressure to detect leaks in the piping network. In a dry pipe fire protection sprinkler system, a pressurized gas, such as air, in the sprinkler system piping network keeps a levered valve closed to hold water back from the piping network. If a sprinkler head in a dry pipe fire protection sprinkler system is actuated by heat, the pressurized gas is discharged from the piping network thereby reducing gas pressure in the piping network. This allows the levered valve to open and water to enter the piping network to be discharged through the open sprinkler head(s) to apply water to extinguish the fire. Dry fire protection sprinkler systems are typically used in areas subject to freezing temperatures as well, as areas where water is undesirable, such as data centers, museums, and the like.

SUMMARY OF THE INVENTION

Corrosion in wet pipe fire protection sprinkler systems can occur as a result of the draining and subsequent refilling of the system with water. Oxygen gets trapped in the water as dissolved oxygen. Oxygen combines with the metal of the pipe network to form an oxide, known as rust. In black steel piping, the oxide is referred to as "red rust" and, in galvanized steel piping, it is referred to as "white rust." Because of code requirements, it may be necessary to repeatedly drain and refill the system, compounding the corrosion potential. However, some forms of corrosion occur in portions of the system where oxygen exists in a much lower concentration, such as under layers of rust that has flaked off the sides of the pipe and rests on the bottom of the pipe in gasket seams and in the troughs of threaded pipe sections. Such corrosion, known as oxygen cell corrosion, can be an aggressive form of corrosion that can cause extensive metal loss from the pipe wall and creates nodules in the pipe wall. Oxygen cell corrosion can form pits and even pinholes in the pipe wall.

Corrosion in dry fire protection sprinkler systems can occur in water that remains in the pipe network, even when in a dry state. For example, water may remain in low points of the pipe network after the system is filled with water and then drained, as is required to occasionally test the system. Also, the air compressor that maintains elevated air pressure in the dry portion of the pipe network can introduce moisture from ambient air, particularly in humid conditions. Because the ratio of water-to-air is so small, there is plenty of oxygen available to make the corrosion process ongoing. As with wet pipe fire protection sprinkler systems, oxygen cell corrosion takes place in dry fire protection sprinkler systems.

A fire protection sprinkler system and method of monitoring corrosion in a fire protection sprinkler system, according to an aspect of the invention, includes a pipe network and at least one sprinkler connected with said pipe network. A corrosion monitor assembly is provided in the pipe network that includes at least one metal coupon and an oxygen depletion area defined on a surface portion of the coupon. A mounting member positions the corrosion monitor assembly to be at least partially covered with water when the sprinkler system is in an operative state.

The oxygen depletion area may be defined by a non-metal material abutting the surface portion of the coupon. The non-metal material may be a polymeric material, such as polytetrafluoroethylene (PTFE). The corrosion monitor assembly may include another metal coupon and another oxygen depletion area defined on a surface portion of the another coupon. The oxygen depletion area on the surface portion of the another coupon may be defined by a non-metal material abutting said surface portion of said another coupon. Opposite sides of a common non-metal material may abut the surface portions of the coupon and the another coupon. The coupon and the another coupon may be made from metals that are the same or from different metals. The metals may be chosen from galvanized steel, copper, brass, austenitic steel and mild steel.

The sprinkler system may be a wet pipe sprinkler system, in which case the mounting member positions the corrosion monitor assembly to extend across at least half of a diameter of the pipe network. The sprinkler system may be a dry fire protection sprinkler system; in which case, the mounting member positions the corrosion monitor assembly to be at a low point or dammed area in said pipe network where trapped water will normally collect. This water collection area may be created in the locations where the metal coupons are installed in the piping network or in a corrosion monitoring assembly. In this manner, the corrosion monitor assembly is covered by water, even when the pipe network is drained of water. The metal coupon(s) may be elongated in a particular direction and the mounting member positions the corrosion monitor assembly with the particular direction generally parallel to the wall.

A fire protection sprinkler system and method of monitoring corrosion in a fire protection sprinkler system, according to another aspect of the invention, includes a pipe network and at least one sprinkler connected with the pipe network. A corrosion monitor assembly is provided in said pipe network that is made up of at least two metal coupons and a non-metal material between the coupons. A mounting member positions the corrosion monitor assembly to be at least partially covered with water when the sprinkler system is in an operative state.

These and other objects, advantages and features of this invention will become apparent upon review of the following specification in conjunction with the drawings.

DESCRIPTION OF THE PREFERRED EMBODIMENT

Figure 1:
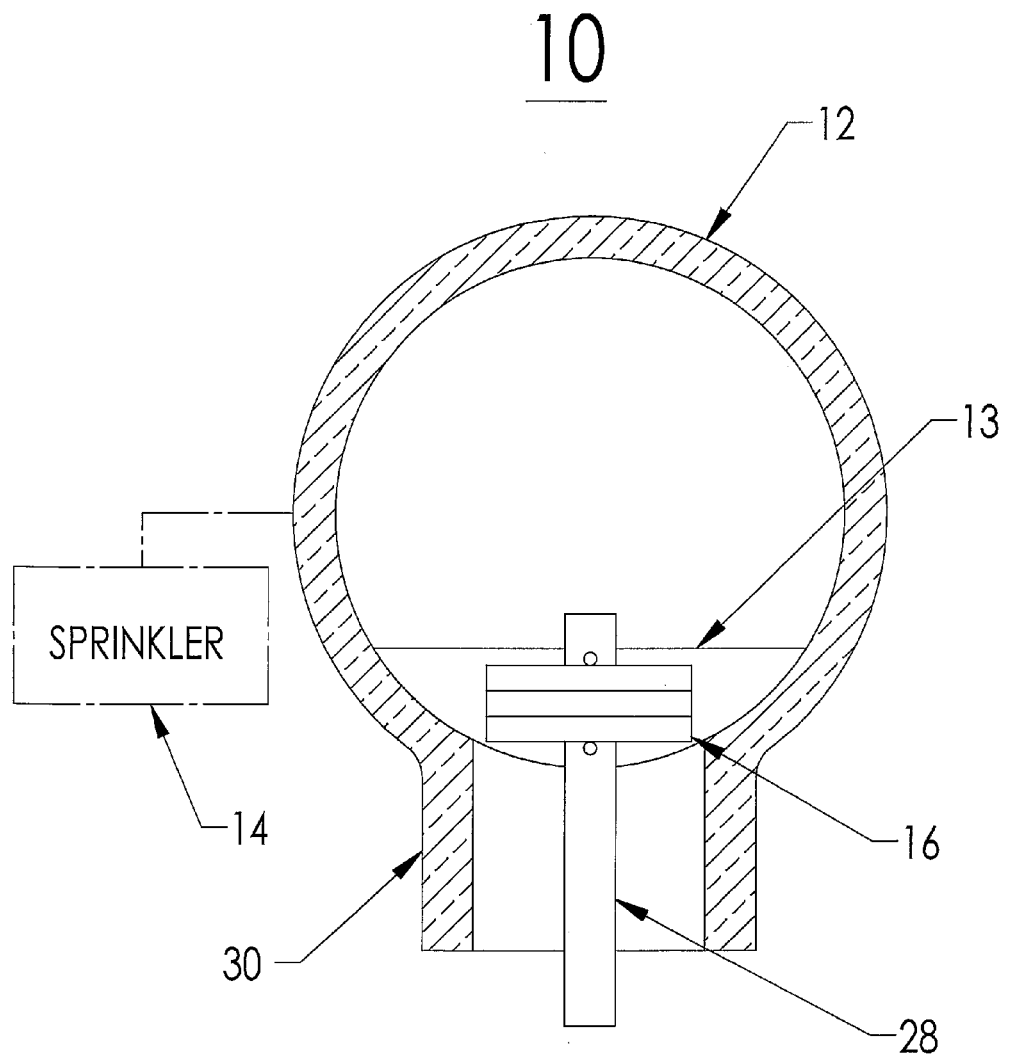
FIG. 1 is a cross-sectional view of a pipe network of a dry fire protection sprinkler system illustrating a corrosion monitor assembly mounted therein.
Figure 2:
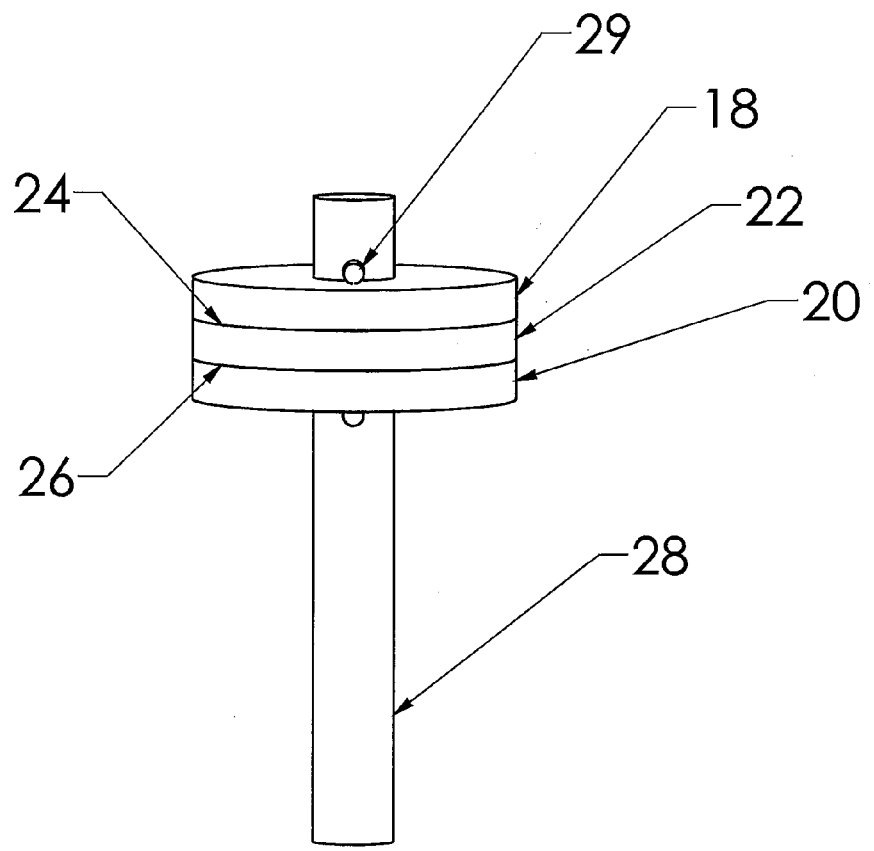
FIG. 2 is an enlarged view of the corrosion monitor assembly in FIG. 1.

Referring now to the drawings and the illustrative embodiments depicted therein, dry fire protection sprinkler system 10 includes a pipe network 12 and a plurality of sprinkler heads 14 connected with pipe network 12. The details of a dry sprinkler system are well known in the art and will not be repeated herein. Suffice it to say that a dry pre-action fire protection sprinkler system includes either an electrically or pneumatically operated valve (not shown). A dry pipe fire protection sprinkler system includes a levered air pressure operated valve. Either type valve keeps water out of pipe network 12 until a fire condition is detected. Once the valve is open, pipe network 12 is flooded with water which will be discharged from one or more of the sprinkler heads 14 when a fuse in the sprinkler head is actuated by the heat from the fire. As previously set forth, dry pre-action fire protection sprinkler systems may optionally include maintenance air supplied to the pipe network to facilitate detection of leaks in the systems. When the valve is closed in either a dry pipe or a dry pre-action fire protection sprinkler system having maintenance air, an air compressor (not shown) keeps an elevated pressure in pipe network 12. Although it is intended that pipe network 12 be generally emptied of water when not triggered by a fire condition, it is common for water to be trapped in pipe network 12. Pipe network 12 must periodically be filled with water in order to test the system. Even though the pipe network is drained after the test, some of the water remains in low spots in the piping network, in crevices of joints, and the like. Also, the air compressor (not shown) that maintains a positive air pressure in pipe network 12 tends to introduce moisture from condensation in the air that is drawn by the compressor.

In order to monitor corrosion that occurs in dry fire protection sprinkler system 10, a water collection area 13 is defined in pipe network 12 and a corrosion monitor assembly 16 is positioned in the water collection area. Water collection area 13 may be defined by a dam defined within pipe network 12 such that water collects and remains behind the dam when the network is drained. In the illustrated embodiment, water collection area 13 is defined by a coupling 30 that is larger than corrosion monitor assembly 16 and forms a tee extending downwardly from pipe network 12. A mounting member 28, which may be made from an electrically non-conductive material, such as a polymeric material, such as nylon, or the like, mounts corrosion monitor assembly 16 in the water collection area. A fastener, which may be made from an electrically non-conductive material, such as a nylon screw 29, holds corrosion monitor assembly 16 to mounting member 28. Water collection area 13 is sized such that, with water drained from pipe network 12, corrosion monitor assembly 16 will be at least partially covered by water. In the illustrated embodiment, corrosion monitor assembly 16 will be covered by approximately one-half inch of water when pipe network 12 is drained. However, a greater or lesser amount may be provided. Corrosion monitoring assembly 16 may be mounted to any portion of the pipe network including to a corrosion monitoring station of the type disclosed in US Pat. Application Publication 2004/0231862 A1, the disclosure of which is hereby incorporated herein by reference.

Corrosion monitor assembly 16 includes a first metal coupon 18, a second metal coupon 20 and a non-metal material 22 between metal coupons 18, 20. Metal coupons 18, 20 are generally planar in shape and are mounted to be parallel to the bottom surface of pipe network 12. In the illustrated embodiment, non-metal material 22 is a polymeric material, such as polytetrafluoroethylene (PTFE), which is marketed under the Teflon® brand. However, other polymeric materials and even other non-metal materials may find application. Non-metal material 22 produces an oxygen depletion area 24 at the interface between material 22 and first metal coupon 18. Non-metal material 22 produces an oxygen depletion area 26 at the interface between material 22 and second metal coupon 20. Oxygen depletion areas 24, 26 are zones which are substantially depleted of oxygen. Oxygen depletion areas 24, 26 are formed by contact between non-metal material 22 and respective coupons 18, 20 without substantial air space. They endeavor to create an environment at coupons 18, 20 that is sensitive to oxygen cell corrosion. This is the type of corrosion that takes place in a lower concentration of oxygen as may occur, for example, under flakes of metal oxides that come off the sides of pipes and collect on the bottom of the pipe. Such oxygen depleted corrosion is capable of creating nodules in the pipe and to create pits that eventually form pin-holes in the pipe that leads to system failure. Thus, corrosion monitor assembly 16 is more sensitive to oxygen cell corrosion and thereby capable of monitoring oxygen cell corrosion as well as conventional corrosion.

As an example, dry fire protection sprinkler systems have an air compressor that is operated to maintain a pressure level in the pipe network. If the air compressor introduces moisture to the pipe network, resulting in the formation of pinholes in the pipe, the compressor may operate more frequently to overcome leakage in the system created by the pinholes. This results in an even greater amount of moisture being introduced by the compressor. This may result in a positive feedback loop that leads to eventual total failure of the pipe network resulting in a costly replacement.

As another example, another type of oxygen depletion area occurs under gaskets where pipes are joined together. This may also be referred to as crevice corrosion. Oxygen depletion areas 24, 26 are capable of monitoring occurrence of such crevice corrosion.

In addition to being sensitive to oxygen depletion corrosion, corrosion monitor assembly 16 is also capable of monitoring corrosion occurring at the interface between the residual water in pipe network and the air retained in the pipe. At the air/water interface in a dry fire protection sprinkler system, the concentration of dissolved oxygen is at a high level. Unlike wet pipe fire protection sprinkler systems in which the oxygenation of the metal in the pipe network may ultimately deplete most of the available oxygen in the system, there is sufficient oxygen in the air present in the pipe network of a dry fire protection sprinkler system to allow corrosion to continue indefinitely. The use of first and second metal coupons 20, 22 provides for the monitoring of corrosion resulting from dissolved oxygen at the air/water interface because water collection area 13 ensures that corrosion monitor assembly 16 will be under water even after pipe network 12 is drained to be placed in service. This provides different readings to account for changed conditions over time.

In the illustrated embodiment, metal coupons 18 and 20 may be made of the same material or different materials. Coupons 18, 20 may be made, for example, from galvanized steel, copper, brass, austenitic steel, mild steel, and the like. One or both of the coupons may be made from the same material as pipe network 12. This allows the same type of corrosion as occurs in the pipe network to be monitored. Also, by having metal coupons 18, 20 of the same material, corrosion may be monitored continuously even if the upper most coupon is occasionally above the water level. However, coupons 18, 20 may be of different metals. This would allow monitoring for more than one metal that may be present in pipe network 12. Also, it would allow a common corrosion monitor assembly to be used for different types of pipe network by providing for a metal that would be used for more than one type of pipe network. Also, one of the coupons may be used for other purposes in the fire protection sprinkler system, such as to dispense zinc, such as from a galvanized steel coupon. The zinc in the water may act against microbiological influenced corrosion (MIC) at high enough levels.

In use, corrosion monitor assembly 16 may be periodically removed and evaluated. This evaluation may be carried out by reweighing the coupons to determine weight loss that has occurred since the last evaluation. Additionally, metal coupons 18, 20 can be evaluated to determine if there is any evidence of corrosion in the oxygen depletion area by examining (i) the number of pits, (ii) the size of the pits (shape and diameter), (iii) the depth of the pits, (iv) the location of the pits on the coupon, and the like. Alternatively, instead of periodically removing corrosion monitor assembly 16 for inspection, it may be used in combination with a corrosion monitor probe of the type disclosed in US Pat. Application Publication No. 2009/0068060 A1, the disclosure of which is hereby incorporated herein by reference. Such corrosion monitor probe includes at least one point of weakness, wherein corrosion of the point of weakness causes a change in pressure in an interior chamber of the monitor which change can be used to provide a signal alerting monitoring personnel. In such an embodiment, the corrosion monitor probe provides an indication that corrosion has occurred to alert maintenance personnel to remove and evaluate corrosion monitor assembly 16 for a more accurate assessment of the nature and severity of the corrosion.

Figure 3:
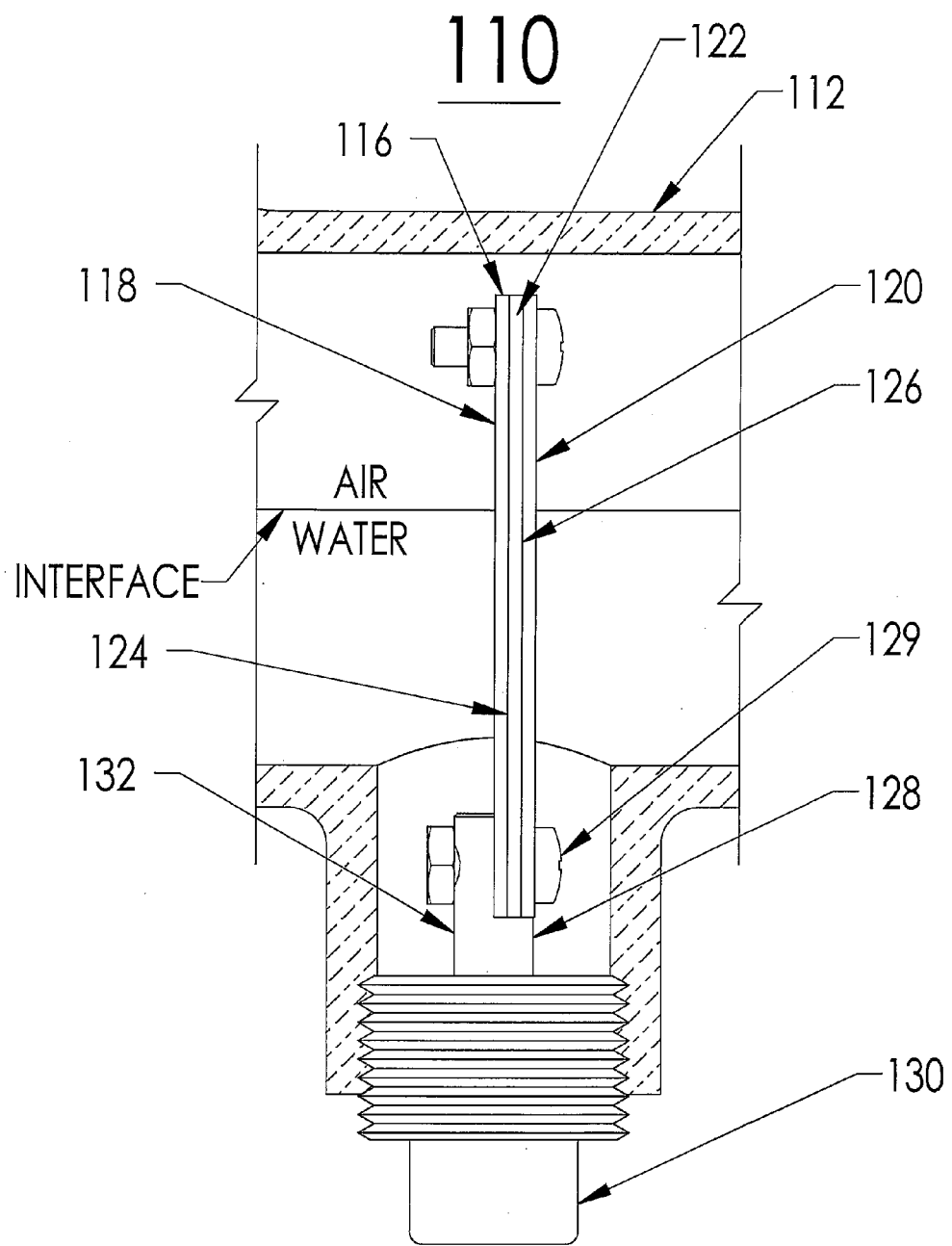
FIG. 3 is a cross-sectional view of a pipe network of a wet type fire protection sprinkler system illustrating a corrosion monitor assembly mounted therein.

In an alternative embodiment, a fire protection sprinkler system 110 is a wet pipe fire protection monitoring system (FIG. 3) and includes a corrosion monitor assembly 116 that is positioned in a pipe network 112 by a mounting member 128. Corrosion monitor assembly 116 is made up of a first metal coupon 118, a second metal coupon 120 and a non-metal material 122 between coupons 118 and 120. This defines an oxygen depletion area, or crevice corrosion zone, 124 between non-metal material 122 and first metal coupon 118. This also defines an oxygen depletion area, or crevice corrosion zone, 126 between non-metal material 122 and second metal coupon 120. Mounting member 128 may include a coupling 130 that extends downwardly from pipe network 120 and a stem 132 that elevates corrosion monitor assembly sufficiently to span the air/water interface within pipe network 112. This may be accomplished in the illustrated embodiment, by corrosion monitoring assembly 116 extending across at least half of a diameter of the pipe in pipe network 112 in which monitoring assembly 116 is located. An electrically non-conductive fastener, such as polymeric fasteners 129, may be used to fasten coupons 118, 120 together and to mounting member 128. Similar fasteners may be used to clamp upper portions of coupons 118, 120 against non-metal material 122. The purpose of using electrically non-conductive fasteners is to avoid conducting a galvanic current between coupons 118, 120.

Corrosion monitor assembly 116 is for the purpose of providing sensitivity to oxygen corrosion, as well as conventional corrosion, in a wet pipe fire sprinkler system. Oxygen corrosion should occur in oxygen depletion areas 124, 126 thereby allowing the corrosion to be detected and evaluated in the manner previously described. In wet pipe fire protection sprinkler system, such oxygen corrosion may occur beneath rust flakes that have collected at the bottom of pipes or under gaskets that join adjacent pipe sections, or the like. By detecting the oxygen corrosion, it may be possible to treat pipe network 12 with a corrosion inhibitor to deter further corrosion, or the like. Coupons 118, 120 may be made from a variety of metals, such as galvanized steel, copper, brass, austenitic steel, mild steel, and the like. As with coupons 18, 20, coupons 118, 120 may be made from the same metal or different metals. Because the coupons are separated by a non-conductive material, there is no cathodic current generated between the coupons even if different metals are used.

Although illustrated with two metal coupons separated by a non-metal layer, it should be understood that certain advantages may be achieved from one metal coupon in contact with a non-metal layer thus defining an oxygen depletion area or crevice corrosion zone. Also, more than three coupons may be used, each pair separated by a non-metal material thus defining more than two oxygen depletion areas or crevice corrosion zones.

Changes and modifications in the specifically described embodiments can be carried out without departing from the principles of the invention which is intended to be limited only by the scope of the appended claims, as interpreted according to the principles of patent law including the doctrine of equivalents.

The embodiments of the invention in which an exclusive property or privilege is claimed are defined as follows:

1. A fire protection sprinkler system, comprising:
   a pipe network and at least one sprinkler connected with said pipe network; and
   a corrosion monitor assembly in said pipe network, said corrosion monitor assembly comprising at least one metal coupon and a layer of non-metal material defining an oxygen depletion area on a surface portion of said at least one metal coupon; and
   a mounting member that positions said at least one metal coupon and said layer of non-metal material to be at least partially covered with water in said pipe network when said sprinkler system is in an operative state.

2. The sprinkler system as claimed in 1 wherein said non-metal material comprises a polymeric material.

3. The sprinkler system as claimed in claim 2 wherein said polymeric material comprises PTFE.

4. The sprinkler system as claimed in claim 1 including another metal coupon having a surface portion.

5. The sprinkler system as claimed in claim 4 wherein opposite sides of the layer of non-metal material abuts said surface portions of said at least one metal coupon and said another metal coupon.

6. The sprinkler system as claimed in claim 4 wherein said at least one metal coupon and said another metal coupon are made from metals that are the same.

7. The sprinkler system as claimed in claim 4 wherein said at least one metal coupon and said another metal coupon are made from different metals.

8. The sprinkler system as claimed in claim 6 wherein said metals comprise at least one chosen from galvanized steel, copper, brass, austenitic steel and mild steel.

9. The sprinkler system as claimed in claim 1, wherein the sprinkler system comprises a wet pipe sprinkler system having an air/water interface in the pipe network, and wherein said mounting member positions said corrosion monitor assembly to extend across the air/water interface of said pipe network.

10. The sprinkler system as claimed in claim 1, wherein the sprinkler system comprises a dry fire protection sprinkler system, wherein said mounting member positions said corrosion monitor assembly to be located at a low point in said pipe network such that said corrosion monitor assembly is covered by water when said pipe network is substantially drained of water.

11. The sprinkler system as claimed in claim 10 wherein said at least one metal coupon is elongated in a particular direction and wherein said mounting member positions said corrosion monitor assembly with said particular direction generally parallel to a pipe wall or generally perpendicular to a pipe wall.

12. A fire protection system corrosion monitor assembly for use in a fire protection sprinkler system having a pipe network and at least one sprinkler connected with said pipe network, said corrosion monitor assembly comprising:
at least one metal coupon having a size and shape that is configured to fit within the pipe network;
a layer of non-metal material defining an oxygen depletion area on a surface portion of said at least one metal coupon; and
a mounting member that positions said at least one metal coupon and said layer of non-metal material to be at least partially covered with water when said sprinkler system is in an operative state.

13. A method of monitoring corrosion in a fire protection sprinkler system having a pipe network and at least one sprinkler connected with said pipe network, said method comprising:
providing a corrosion monitoring assembly comprising at least one metal coupon having a size and shape that is configured to fit within the pipe network and a layer of non-metal material defining an oxygen depletion area on a surface portion of said at least one metal coupon; and
positioning said corrosion monitoring assembly in the pipe network in a manner that said at least one metal coupon and said layer of non-metal material are at least partially covered with water when said sprinkler system is in an operative state.

14. The method as claimed in 13 wherein said non-metal material comprises a polymeric material.

15. The method as claimed in claim 14 wherein said polymeric material comprises PTFE.

16. The method as claimed in claim 13, wherein the corrosion monitoring assembly comprises another metal coupon having a surface portion.

17. The method as claimed in claim 16 wherein opposite sides of the layer of non-metal material abuts said surface portions of said at least one metal coupon and said another metal coupon.

18. The method as claimed in claim 16 wherein said at least one metal coupon and said another metal coupon are made from metals that are the same.

19. The method as claimed in claim 16 wherein said at least one metal coupon and said another metal coupon are made from different metals.

20. The method as claimed in claim 18 wherein said metals comprise at least one chosen from galvanized steel, copper, brass, austenitic steel and mild steel.

21. The method as claimed in claim 13, wherein the sprinkler system is a wet pipe sprinkler system having an air/water interface in the pipe network, wherein said positioning includes positioning said corrosion monitor assembly to extend across the air/water interface of said pipe network.

22. The method as claimed in claim 13, wherein the sprinkler system is a dry fire protection sprinkler system, wherein said positioning includes positioning said corrosion monitor assembly to be at a low point in said pipe network so that said corrosion monitor assembly is at least partially covered by water when said pipe network is substantially drained of water.

23. The method as claimed in claim 22 wherein said at least one metal coupon is elongated in a particular direction and wherein said positioning includes positioning said corrosion monitor assembly with said particular direction generally parallel to a pipe wall or generally perpendicular to a pipe wall.

24. A fire protection sprinkler system, comprising:
a pipe network and at least one sprinkler connected with said pipe network; and
a corrosion monitor assembly in said pipe network, said corrosion monitor assembly comprising at least two metal coupons and a layer of non-metal material between said coupons, the layer of non-metal material defining an oxygen depletion area between the layer of non-metal material and one of the at least two metal coupons; and
a mounting member that positions said at least two metal coupons and said layer of non-metal material to be at least partially covered with water in said pipe network when said sprinkler system is in an operative state.

25. A fire protection system corrosion monitor assembly for use in a fire protection sprinkler system having a pipe network and at least one sprinkler connected with said pipe network, said corrosion monitor assembly comprising:
at least two metal coupons having a size and shape that is configured to fit within the pipe network; and
a layer of non-metal material between said coupons, the layer of non-metal material defining an oxygen depletion area between the layer of non-metal material and one of the at least two metal coupons; and
a mounting member that positions said coupons and said layer of non-metal material to be at least partially covered with water when said sprinkler system is in an operative state.

26. A method of monitoring corrosion in a fire protection sprinkler system having a pipe network and at least one sprinkler connected with said pipe network, said method comprising:

providing a corrosion monitoring assembly comprising at least two metal coupons having a size and shape that is configured to fit within the pipe network and a layer of non-metal material between said coupons, the layer of non-metal material defining an oxygen depletion area between the layer of non-metal material and one of the at least two metal coupons; and positioning said corrosion monitoring assembly in the pipe network so that said coupons and said layer of non-metal material are at least partially covered with water when said sprinkler system is in an operative state.

* * * * *